US00PP31675P2

(12) United States Plant Patent
Spruyt

(10) Patent No.: US PP31,675 P2
(45) Date of Patent: Apr. 14, 2020

(54) ***ECHINACEA* PLANT NAMED 'JS ENGELTJE'**

(50) Latin Name: *Echinacea purpurea*
Varietal Denomination: JS Engeltje

(71) Applicant: Spruyt Select GCV, Buggenhout (BE)

(72) Inventor: Jan Spruyt, Buggenhout (BE)

(73) Assignee: SPRUYT SELECT GCV, Buggenhout (BE)

( * ) Notice: Subject to any disclaimer, the term of this patent is extended or adjusted under 35 U.S.C. 154(b) by 0 days.

(21) Appl. No.: 16/350,934

(22) Filed: Feb. 1, 2019

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
See application file for complete search history.

*Primary Examiner* — Anne Marie Grunberg
(74) *Attorney, Agent, or Firm* — Penny J. Aguirre

(57) ABSTRACT

A new cultivar of hybrid *Echinacea* plant named 'JS Engeltje' characterized by its upright growth habit with strong stems that don't flop, its healthy foliage, floriferous and long flowering habit; blooming from July to November with inflorescences that emerge one after another (rather than simultaneously), its inflorescences that bloom at different heights to give the plant a unique wild look, its inflorescences with ray florets that are purple-pink and white in color (bicolor), and its high endurance to wind, cold, heat and sun.

2 Drawing Sheets

Botanical classification: *Echinacea purpurea.*
Variety denomination: 'JS Engeltje'.

BACKGROUND OF THE INVENTION

The present invention relates to a new and distinct cultivar of *Echinacea* of hybrid origin and will be referred to hereafter by its cultivar name 'JS Engeltje'. 'JS Engeltje' is an herbaceous perennial grown for landscape and container use.

'JS Engeltje' was discovered by the Inventor as a chance seedling in a production field plot in Buggenhout, Belgium in 2013. The parentage is unknown.

Asexual propagation of the new cultivar was first accomplished by tissue culture using vegetative shoot meristematic tissue under the direction of the Inventor in Buggenhout, Belgium. Asexual propagation by tissue culture has determined that the characteristics of the new cultivar are stable and are reproduced true to type in successive generations.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1).

SUMMARY OF THE INVENTION

The following traits have been repeatedly observed and represent the characteristics of the new cultivar. These attributes in combination distinguish 'JS Engeltje' as unique cultivar of *Echinacea.*

1. 'JS Engeltje' exhibits an upright growth habit with strong stems that don't flop.
2. 'JS Engeltje' exhibits healthy foliage.
3. 'JS Engeltje' exhibits a floriferous and long flowering habit; blooming from July to November with inflorescences that emerge one after another (rather than simultaneously).
4. 'JS Engeltje' exhibits inflorescences that bloom at different heights to give the plant a unique wild look.
5. 'JS Engeltje' exhibits inflorescences with ray florets that are purple-pink and white in color (bicolor).
6. 'JS Engeltje' exhibits high endurance to wind, cold, heat and sun.

'JS Engeltje' can be most closely compared to the *Echinacea* cultivars 'Fountain Pink Eye', (not patented) and 'Pink Tip' (not patented). 'Fountain Pink Eye' is similar to 'JS Engeltje' in having small leaves and flowers with similar colored ray florets. 'Fountain Pink Eye' differs from 'JS Engeltje' in a shorter blooming season, flowers with similar colored ray florets, and leaves that are less glossy. 'Pink Tip' is similar to 'JS Engeltje' in having flowers with similar colored ray florets. 'Pink Tip' differs from 'JS Engeltje' in having a shorter blooming season and in having flowers with ray florets that have a smaller purple-pink area.

BRIEF DESCRIPTION OF THE DRAWINGS

The accompanying colored photographs illustrate the overall appearance and distinct characteristics of the new *Echinacea*. The photographs were taken of a 1.5-year-old plant of the new cultivar as field grown in Buggenhout, Belgium (placed in a 34-cm container for the photographs with some drying of leaves due to moist stress).

The photograph in FIG. 1 illustrates the overall habit and appearance of 'JS Engeltje' in bloom.

Figure 1:
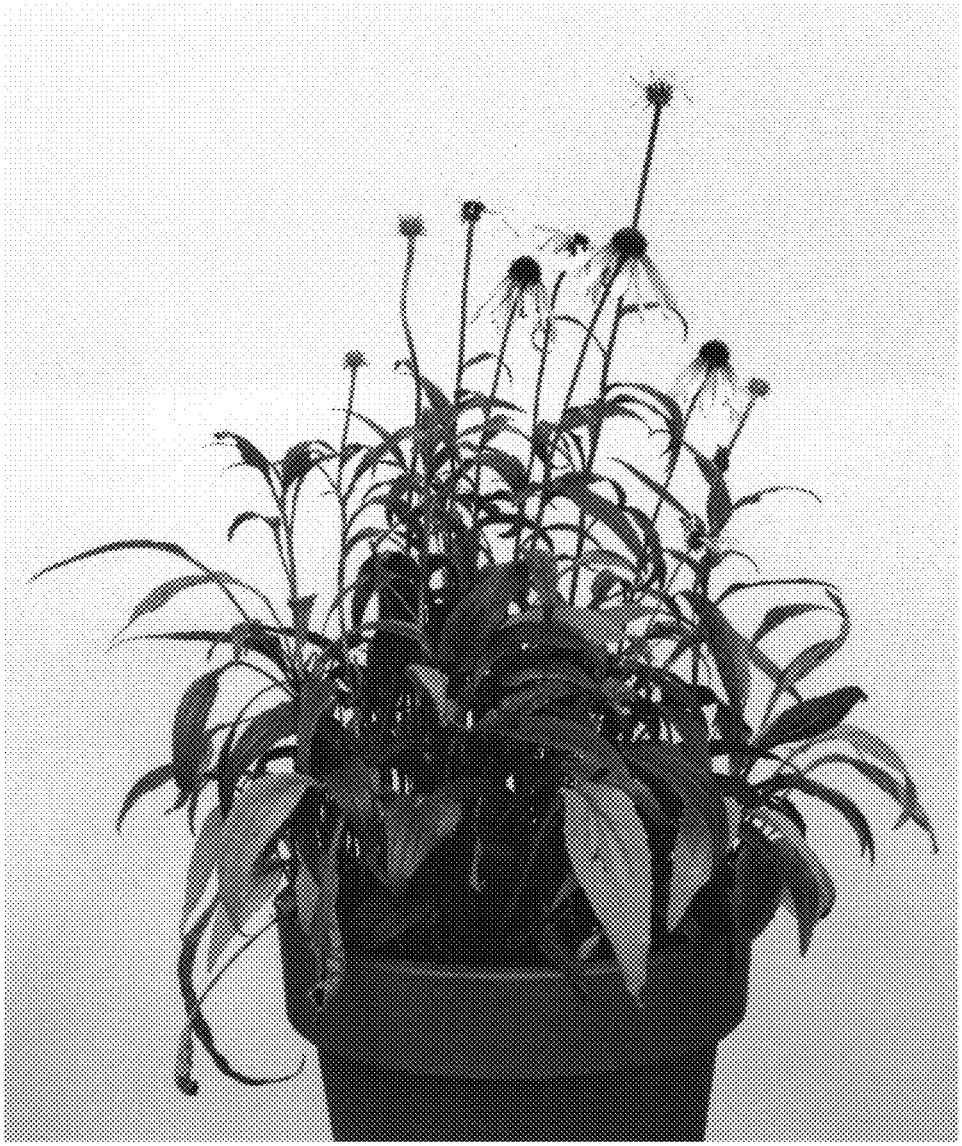
Figure 2:
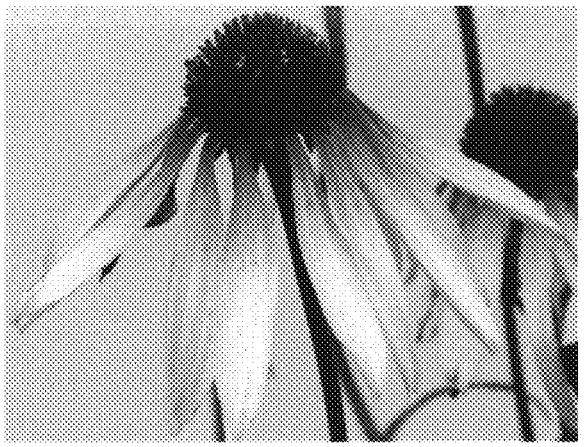

The photograph in FIG. 2 provides a close-up view of the inflorescences of 'JS Engeltje'.

Figure 3:
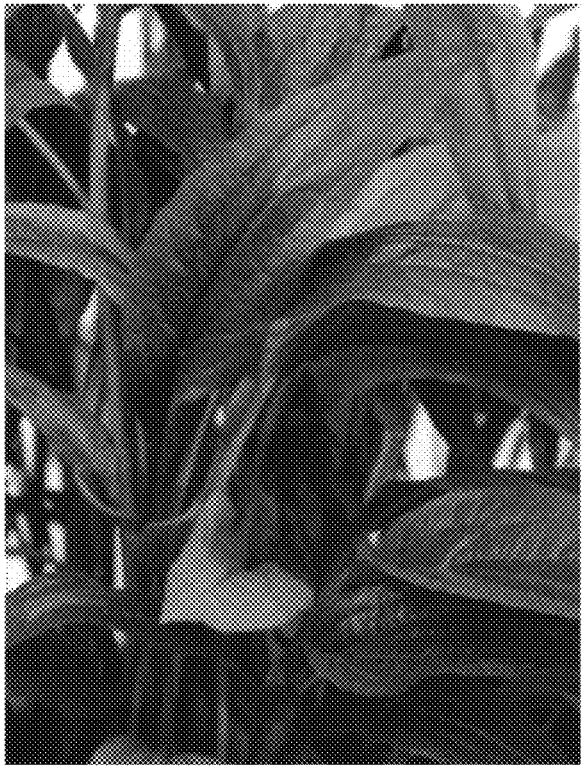

The photograph in FIG. 3 provides a close-up view of the mature foliage of 'JS Engeltje'.

The colors in the photographs are as close as possible with the photographic and printing technology utilized and color values cited in the detailed botanical description accurately describe the colors of the new *Echinacea*.

DETAILED BOTANICAL DESCRIPTION

The following is a detailed description of 1.5-year-old plants of the new cultivar as field grown in Buggenhout, Belgium. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Blooms from early July to November, in Buggenhout, Belgium.

*Plant type.*—Herbaceous perennial.

*Plant habit.*—Upright with strong stems that do not lodge.

*Height and spread.*—70 to 80 cm in height and an average of 50 cm in spread as a mature plant in the landscape.

*Cold hardiness.*—At least in U.S.D.A Zone 3.

*Disease and pests.*—No susceptibility and resistance to diseases or pests has been identified but plants have been observed to have healthy foliage.

*Environmental stresses.*—Has shown a high endurance to wind, cold, heat and sun.

*Root description.*—Fibrous and fine, 158D in color.

*Propagation.*—Tissue culture using meristem tissue.

*Growth rate.*—Moderate to high.

*Root development.*—An average of 4 weeks to initiate roots in tissue culture and an average of 14 weeks to produce a young plant.

Stem description:

*Shape.*—Rounded.

*Stem color.*—Young branches; 144A, mature branches; marbled N200A.

*Stem size.*—An average of 43.2 cm in length, 4 mm in diameter.

*Stem strength.*—Very strong.

*Stem aspect.*—Primary branches grow in an average angle of 15° from the base (0°=vertical).

*Stem surface.*—Moderately covered with short strigose hairs average of 0.5 mm in length and 155A in color.

*Stem number.*—Average of 3 primary branches.

*Internode length.*—Average of 6.2 cm in length.

*Branching.*—Main flowering stem grows from base.

Foliage description:

*Leaf shape.*—Basal; ovate to narrow ovate, cauline; narrow ovate.

*Leaf division.*—Simple.

*Leaf base.*—Attenuate to short attenuate.

*Leaf apex.*—Basal and cauline; narrow acute.

*Leaf venation.*—Pinnate, basal and cauline; upper surface 148C to 148D, lower surface 144C.

*Leaf margins.*—Basal and cauline; coarsely un-deeply serrate and very slightly undulate to non-undulate.

*Leaf attachment.*—Petiolate.

*Leaf arrangement.*—Alternate.

*Leaf size.*—Basal; average of 20.8 cm in length and 4.4 cm in width, cauline; 11.5 cm in length, 2.4 cm in width.

*Leaf color.*—Basal and cauline; young upper surface; 143A, young lower surface; between 146B, mature upper surface; NN137A, mature lower surface; 146A and 147B.

*Leaf surface.*—Basal and cauline; upper surfaces are matte, lower surface slightly glossy, both surfaces rough to the touch due to pubescence and densely covered with short strigose hairs an average of 0.3 mm in length and too small to measure color.

*Petioles.*—Basal; 20.2 cm in length, cauline; 6.1 cm in length, both are v-shaped, 2 mm in diameter (horizontal) and 3 mm in diameter (vertical), color upper surface 144B, fading to the proximal end 60A, color lower surface 144A, fading to the proximal end 64C, both surfaces glossy and glabrous.

Flower description:

*Type.*—Terminal capitulum consisting of ray florets and disc florets, inflorescences emerge in succession and at different heights in bloom.

*Capitulum number.*—An average of 1 per stem, 10 per plant.

*Lastingness of inflorescence.*—Average of 2 weeks, ray florets self-cleaning.

*Capitulum size.*—Matures to about 6.7 cm in height and 9.2 cm in diameter, disc is an average of 2.8 cm in diameter.

*Fragrance.*—None.

*Involucral bracts or phyllary.*—Rotate, 48 arranged in 3 overlapping rows, average of 9 mm in length and 2.5 mm in width, cuneate base, acute apex, ovate in shape, color upper surface NN137B, color lower surface NN137B to NN137C, upper surface texture; matte, lower surface texture; matte and moderately pubescent with very short strigose hairs an average of 0.3 mm in length and too small to measure color., margins are entire and moderately pubescent with very short strigose hairs, an average of 0.3 mm in length and too small to measure color.

*Buds.*—Flattened globular in shape with immature ray florets near vertical, an average of 2 cm in length and 2.3 cm in diameter, 146A in color at base with immature ray florets 145B and fading at the apex to 143B and tinged with 177D on lower half.

*Peduncle.*—Strong, terminal is an average of 15.3 cm in length, an average of 3 mm in diameter, upright aspect, 148A and marbled 200C in color, surface is moderately glossy and moderately covered with short strigose hairs, 0.3 mm in length and too small to measure color.

*Ray florets.*—Rotate around disc in 1 row, unfused, average of 14 per inflorescence, oblanceolate in shape, average of 5.7 cm in length and 1.3 cm in width, emarginate to praemorse to deeply emarginate apex, cuneate base, entire margin, outward, average angle of −55° to horizontal, color; upper surface when opening 150D and 155D, base 54D, lower surface when opening 160D, base tinged 47D, upper surface when fully open between 155C and 157D, outer tip in between 145C to 145D, fading towards the base 59B to 59C, lower surface when fully open 150D, outer tip 144C, fading towards the base to 59C, surface texture; upper surface glabrous, moderately velvety and matte, lower surface glabrous, slightly glossy.

*Disk florets.*—Numerous, average of 160, arranged spirally on disc, tubular appearance, upright to outward aspect, apex is acute on upper 10% that is free, fused (tubular) base, entire margin, average of 1.2 cm in length and 3 mm in width, upper and lower surface textures are glabrous and moderately glossy, color; when opening upper and lower surface 177D, mid-section and base 146D, when fully open upper and lower surface 187B, mid-section 187C to 187D and base tinged 147D.

*Disk spines.*—Average of 160, acicular in shape, acute apex, attenuate base, smooth, glabrous and glossy surface, color is 53A at apex, blending to 28A to 28B, 146B in mid region and 157B at base.

*Receptacle.*—Deltoid in shape, an average of 8 mm in height and 7 mm diameter, and 155A in color with margined 187B.

Reproductive organs (present on disk florets only):

*Gynoecium.*—Pistil; 1, 9 mm in length, style; 6 mm in length and 150C to 150D in color, stigma; unequal decurrent and N186C in color, ovary; 157D in color.

*Androcoecium.*—Stamens; 5, filaments; 3 mm in length and 153D in color, anthers; linear in shape, 3.5 mm in length, N200A to 202A in color, pollen is low in quantity and 23A in color.

*Fruit/seed.*—No seed production has been observed.

It is claimed:

1. A new and distinct cultivar of *Echinacea* plant named 'JS Engeltje' as herein illustrated and described.

* * * * *